United States Patent [19]
Turnbull

[11] Patent Number: 5,273,988
[45] Date of Patent: Dec. 28, 1993

[54] 2-(3,4,4,-TRIFLUOROBUTENYLMERCAPTO) ALKOXY OR NITRO BENZOXAZOYL COMPOUNDS

[75] Inventor: Michael D. Turnbull, Earley, Great Britain

[73] Assignee: Imperial Chemical Industries Plc, London, Great Britain

[21] Appl. No.: 854,144

[22] Filed: Mar. 18, 1992

[30] Foreign Application Priority Data

Apr. 2, 1991 [GB] United Kingdom ............ 9106655
Apr. 2, 1991 [GB] United Kingdom ............ 9106656

[51] Int. Cl.$^5$ ............................................. A01N 43/76
[52] U.S. Cl. .......................................... 514/375; 548/221
[58] Field of Search ........................... 514/375; 548/221

[56] References Cited

U.S. PATENT DOCUMENTS

| | | | |
|---|---|---|---|
| 2,630,381 | 3/1953 | Schlensinger | 548/221 |
| 2,871,156 | 1/1959 | Hymas | 514/375 |
| 2,922,794 | 1/1960 | Model | 548/221 |
| 3,153,653 | 10/1964 | Raasch | 548/221 |
| 3,780,050 | 12/1973 | Brokke | 548/221 |
| 4,328,219 | 5/1982 | Mues et al. | 514/375 |
| 4,649,149 | 3/1987 | Gallay et al. | 514/375 |
| 5,102,898 | 4/1992 | Hsu | 514/375 |

FOREIGN PATENT DOCUMENTS

| | | | |
|---|---|---|---|
| 1241754 | 8/1960 | France . | |
| 926455 | 5/1963 | United Kingdom | 514/375 |
| 1413519 | 11/1975 | United Kingdom . | |

OTHER PUBLICATIONS

Chen et al. Jour. Flourine Chem. vol. 51, pp. 21-32 (1991).

Primary Examiner—Donald G. Daus
Attorney, Agent, or Firm—Joel G. Ackerman

[57] ABSTRACT

Compounds of formula (I):

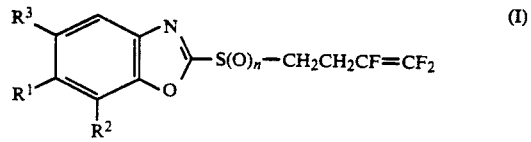

wherein $R^1$, $R^2$ and $R^3$ are independently hydrogen, alkyl, alkenyl, alkynyl, cycloalkyl, alkylcycloalkyl, halogen, haloalkyl, alkoxy, alkenoxy, alkoxyalkyl, haloalkoxy, alkylthio, cyano, nitro, amino, $NR^5R^6$, hydroxy, amino, acylamino, $-CO_2R^4$, or $R^1$ and $R^3$ when taken together form a 5- or 6-membered ring; $R^4$ and $R^6$ are hydrogen or $C_{1-4}$ alkyl; $R^5$ is $C_{1-4}$ alkyl; n is 0 or 1; provided that $R^1$, $R^2$ and $R^3$ are not all hydrogen when n is 0; are useful as nematicides.

9 Claims, No Drawings

2-(3,4,4,-TRIFLUOROBUTENYLMERCAPTO) ALKOXY OR NITRO BENZOXAZOYL COMPOUNDS

The present invention relates to novel benzoxazole derivatives having nematicidal activity, to processes for their preparation, to compositions containing them, and to methods for killing or controlling nematode pests using them.

U.S. Pat. No. 3,780,050 describes 2-(3,4,4-trifluorobutenylthio)-benzoxazole as having nematicidal properties.

According to the present invention there is provided a compound of formula (I) wherein $R^1$, $R^2$ and $R^3$ are independently hydrogen, alkyl, alkenyl, alkynyl, cycloalkyl, alkylcycloalkyl, halogen, haloalkyl, alkoxy, alkenoxy, alkoxyalkyl, haloalkoxy, alkylthio, cyano, nitro, amino, $NR^5R^6$, hydroxy, amino, acylamino, $-CO_2R^4$, or $R^1$ and $R^3$ when taken together form a 5- or 6-membered ring; $R^4$ and $R^6$ are hydrogen or $C_{1-4}$ alkyl; $R^5$ is $C_{1-4}$ alkyl; n is 0 or 1; provided that $R^1$, $R^2$ and $R^3$ are not all hydrogen when n is 0.

When any of $R^1$, $R^2$ and $R^3$ is an alkyl group it can be straight or branched chain and is preferably $C_{1-4}$ alkyl, in particular, methyl, ethyl, propyl, isopropyl, n-butyl, iso-butyl, sec-butyl or tertiary butyl.

When any of $R^1$, $R^2$ and $R^3$ is an alkenyl or alkynyl group it can be straight or branched chain and preferably contains up to 6 carbon atoms, for example, allyl or propargyl.

When any of $R^1$, $R^2$ and $R^3$ is a cycloalkyl or alkylcycloalkyl group, it preferably contains from 3 to 7 carbon atoms, for example, cyclopropyl, cyclopentyl, cyclohexyl or methylcyclopropyl.

When any of $R^1$, $R^2$ and $R^3$ is halogen, it is preferably fluorine or chlorine.

When any of $R^1$, $R^2$ and $R^3$ is a haloalkyl group, the alkyl moiety is preferably $C_{1-4}$ alkyl, for example, trifluoromethyl, trifluoroethyl or pentafluoroethyl.

When any of $R^1$, $R^2$ and $R^3$ is an alkoxy, alkenoxy or alkoxyalkyl group it can be straight or branched chain and preferably contains up to 6 carbon atoms, for example, a methoxy, ethoxy, propoxy, butoxy, butenoxy, methoxymethyl, methoxyethyl or ethoxymethyl group.

When any of $R^1$, $R^2$ or $R^3$ is a haloalkoxy group, it can be straight or branched chain and preferably contains up to 6 carbon atoms, for example, trifluoromethoxy, trifluoroethoxy or pentafluoroethoxy.

When any of $R^1$, $R^2$ and $R^3$ is an alkylthio group, the alkyl preferably contains up to 4 carbon atoms. For example, —S-methyl, —S-ethyl, —S-propyl, S-butyl.

When any of $R^1$, $R^2$ or $R^3$ is $NR^5R^6$, it is preferably $NHCH_3$, $N(CH_3)_2$ or $N(C_2H_5)_2$.

When any of $R^1$, $R^2$ or $R^3$ is acylamino, it is preferably $NHCOCH_3$ or $NCOC_2H_5$.

When any of $R^1$, $R^2$ or $R^3$ is $CO_2R^4$, $R^4$ is preferably hydrogen, methyl or ethyl.

When $R^1$ and $R^3$ are taken together to form a 5- or 6-membered ring, it is preferably a carbocyclic ring, for example, $-(CH_2)_3-$, $-(CH_2)_4-$ or $-CH=CH-CH=CH-$.

Examples of the compounds of formula (I) are set out in Table I.

TABLE I

| COMPOUND NO. | $R^1$ | $R^2$ | $R^3$ | n |
|---|---|---|---|---|
| 1 | $OCH_3$ | H | H | 0 |
| 2 | F | H | H | 0 |
| 3 | H | F | H | 0 |
| 4 | $NO_2$ | H | H | 0 |
| 5 | $NH_2$ | H | H | 0 |
| 6 | $CH_3$ | H | H | 0 |
| 7 | H | F | F | 0 |
| 8 | OH | H | H | 0 |
| 9 | $CO_2CH_3$ | H | H | 0 |
| 10 | $NHCOCH_3$ | H | H | 0 |
| 11 | Cl | H | H | 0 |
| 12 | COOH | H | H | 0 |
| 13 | H | H | H | 1 |
| 14 | F | H | H | 1 |
| 15 | $CH_3$ | H | H | 1 |
| 16 | H | $CH_3$ | H | 0 |
| 17 | H | $CH_2CH=CH_2$ | H | 0 |
| 18 | H | $^cC_3H_5$ | H | 0 |
| 19 | H | Cl | H | 0 |
| 20 | H | CN | H | 0 |
| 21 | H | H | $CH_3$ | 0 |
| 22 | H | H | $CH_2CH=CH_2$ | 0 |
| 23 | H | H | $^cC_3H_5$ | 0 |
| 24 | H | H | Cl | 0 |
| 25 | H | H | CN | 0 |
| 26 | $CH_3$ | H | $CH_3$ | 0 |
| 27 | Cl | H | Cl | 0 |
| 28 | F | H | Cl | 0 |
| 29 | $OCH_3$ | $NHCOCH_3$ | H | 0 |
| 30 | $OCH_3$ | $OCH_3$ | H | 0 |
| 31 | $OCH_3$ | H | $OCH_3$ | 0 |
| 32 | 1-$CH_3-^cC_3H_5$ | H | H | 0 |
| 33 | OH | H | F | 0 |
| 34 | OH | Cl | H | 0 |
| 35 | H | $CO_2CH_3$ | H | 0 |
| 36 | $OCH_2CF_3$ | H | H | 0 |
| 37 | $OCH_2CF_3$ | H | H | 1 |
| 38 | $CH_2OCH_3$ | H | H | 1 |
| 39 | H | $CH_2OCH_3$ | H | 1 |
| 40 | H | H | $CH_3$ | 1 |
| 41 | H | CN | H | 1 |
| 42 | H | —CH=CH—CH=CH— | | 1 |
| 43 | H | —CH=CH—CH=CH— | | 2 |
| 44 | OH | —CH=CH—CH=CH— | | 0 |
| 45 | H | —CH=CH—CH=CH— | | 0 |

The compounds of formula (I) may be further oxidised, perhaps by enzymic metabolism, in the soil to compounds of formula (I) where n is 2.

The compounds of formula (I) where $R^1$, $R^2$ and $R^3$ have the meanings defined above and n is 0 are prepared by reacting a correspondingly substituted benzoxazole of formula (II) with 4-bromo-trifluorobut-1-ene in the presence of a base such as a carbonate, for example, potassium carbonate, and an inert solvent, for example acetone.

Thus, according to a further aspect of the present invention there is provided a process for the preparation of compounds of formula (I) where n is 0 and $R^1$, $R^2$ and $R^3$ have the meanings defined above which comprises reacting a correspondingly substituted compound of formula (II) with 4-bromo-trifluorobut-1-ene in the presence of a base.

The compounds of formula (II) are prepared by reacting a correspondingly substituted 2-aminophenol or a salt thereof, with thiophosgene, in an inert solvent such as diethyl ether or chloroform, and optionally in the presence of a base, such as potassium carbonate, and/or water.

The compounds of formula (I) where any one or more of $R^1$, $R^2$ $R^3$ is alkoxy can alternatively be prepared by reacting the corresponding hydroxy derivative of formula (I) with an alkylating agent, for example dimethyl sulphate.

The compounds of formula (I) where $R^1$, $R^2$ and $R^3$ have the meanings defined above and n is 1 are prepared by oxidising a correspondingly substituted benzoxazole of formula (I) where n is 0. The oxidation is carried out using conventional methods, for example by treatment with a peroxide in an inert organic solvent. Suitable peroxides include organic peroxides such as peroxy carboxylic acids, or their salts, for example, magnesium monoperoxyphthalic acid. Suitable inorganic peroxides include potassium peroxymono-sulphate.

Thus, according to a yet further aspect of the present invention there is provided a process for the preparation of compounds of formula (I) where n is 1 and $R^1$, $R^2$ and $R^3$ have the meanings defined above, which comprises reacting a correspondingly substituted compound of formula (I) when n is 0, with an oxidising agent.

4-bromo-trifluorobut-1-ene can be obtained by conventional methods or from commercial sources.

The compounds of formula (I) are nematicidal and can be used to control nematodes in crop plants. Therefore, in a further aspect of the invention, there is provided a method for killing or controlling nematodes which comprises applying to the locus of the pests or to a plant susceptible to attack by the pest an effective amount of a compound of formula (I) as defined herein.

The term "controlling" extends to non-lethal effects which result in the prevention of damage to the host plant and the limitation of nematode population increase. These effects may be the result of chemical induced disorientation, immobilisation, or hatch prevention or induction. The chemical treatment may also have deleterious effects on nematode development or reproduction.

The compounds of the invention can be used against both plant-parasitic nematodes and nematodes living freely in the soil. Examples of plant-parasitic nematodes are: ectoparasites, for example Xiphinema spp., Longidorus spp. and Trichodorous spp.; semi-endoparasites, for example, Tylenchulus spp.; migratory endoparasites, for example, Pratylenchus spp., Radopholus spp. and Scutellonema spp.; sedentary endoparasites, for example, Heterodera spp., Globodera spp. and Meloidogyne spp.; and stem and leaf endoparasites, for example, Ditylenchus spp., Aphelenchoides spp. and Hirshmaniella spp.

The compounds of the invention can also be used in combating a range of insects and acarids. Examples include Lepidoptera, Diptera, Homoptera and Coleoptera (including Diabrotica i.e. corn rootworms).

In order to apply the compound to the locus of the nematode or to a plant susceptible to attack by the nematode, the compound is usually formulated into a composition which includes in addition to the compound of formula (I) suitable inert diluent or carrier materials, and/or surface active agents. Thus in a further aspect of the invention there is provided a nematicidal composition comprising an effective amount of a compound of formula (I) as defined herein and an inert diluent or carrier material and optionally a surface active agent.

The amount of composition generally applied gives a rate of active ingredient from 0.01 to 10 kg per hectare, preferably from 0.1 to 6 kg per hectare.

The compositions can be applied to the soil, plant or seed, in the form of dusting powders, wettable powders, granules (slow or fast release), emulsion or suspension concentrates, liquid solutions, emulsions, seed dressings, fogging/smoke formulations or controlled release compositions, such as microencapsulated granules or suspensions.

Dusting powders are formulated by mixing the active ingredient with one or more finely divided solid carriers and/or diluents, for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers.

Granules are formed either by absorbing the active ingredient in a porous granular material for example pumice, attapulgite clays, fuller's earth, kieselguhr, diatomaceous earths, ground corn cobs, and the like, or on to hard core materials such as sands, silicates, mineral carbonates, sulphates, phosphates, or the like. Agents which are commonly used to aid in impregnation, binding or coating the solid carriers include aliphatic and aromatic petroleum solvents, alcohols, polyvinyl acetates, polyvinyl alcohols, ethers, ketones, esters, dextrins, sugars and vegetable oils. with the active ingredient. Other additives may also be included, such as emulsifying agents, wetting agents or dispersing agents.

Microencapsulated formulations (microcapsule suspensions CS) or other controlled release formulations may also be used, particularly for slow release over a period of time, and for seed treatment.

Alternatively the compositions may be in the form of liquid preparations to be used as dips, irrigation additives or sprays, which are generally aqueous dispersions or emulsions of the active ingredient in the presence of one or more known wetting agents, dispersing agents or emulsifying agents (surface active agents). The compositions which are to be used in the form of aqueous dispersions or emulsions are generally supplied in the form of an emulsifiable concentrate (EC) or a suspension concentrate (SC) containing a high proportion of the active ingredient or ingredients. An EC is a homogeneous liquid composition, usually containing the active ingredient dissolved in a substantially non-volatile organic solvent. An SC is a fine particle size dispersion of solid active ingredient in water. To apply the concentrates they are diluted in water and are usually applied by means of a spray to the area to be treated.

Suitable liquid solvents for ECs include methyl ketone, methyl isobutyl ketone, cyclohexanone, xylenes, toluene, chlorobenzene, paraffins, kerosene, white oil, alcohols, (for example, butanol), methylnaphthalene, trimethylbenzene, trichloroethylene, N-methyl-2-pyrrolidone and tetrahydrofurfuryl alcohol (THFA).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate,and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

These concentrates are often required to withstand storage for prolonged periods and after such storage, to be capable of dilution with water to form aqueous preparations which remain homogeneous for a sufficient time to enable them to be applied by conventional spray equipment. The concentrates may contain 10–85% by weight of the active ingredient or ingredients. When diluted to form aqueous preparations such preparations may contain varying amounts of the active ingredient depending upon the purpose for which they are to be used.

The compounds of formula (I) may also be formulated as powders (dry seed treatment DS or water dispersible powder WS) or liquids (flowable concentrate FS, liquid seed treatment LS, or CS) for use in seed treatments. In use the compositions are applied to the nematodes, to the locus of the nematodes, to the habitat of the nematodes, or to growing plants liable to infestation by the nematodes, by any of the known means of applying pesticidal compositions, for example, by dusting, spraying, or incorporation of granules.

The compounds of the invention may be the sole active ingredient of the composition or they may be admixed with one or more additional active ingredients such as nematicides or agents which modify the behaviour of nematodes such as hatching factors, insecticides, synergists, herbicides, fungicides or plant growth regulators where appropriate.

Suitable additional active ingredients for inclusion in admixture with the compounds of the invention may be compounds which will broaden the spectrum of activity of the compounds of the invention or increase their persistence in the location of the pest. They may synergise the activity of the compound of the invention or complement the activity for example by increasing the speed of effect or overcoming repellency. Additionally multi-component mixtures of this type may help to overcome or prevent the development of resistance to individual components.

The particular additional active ingredient included will depend upon the intended utility of the mixture and the type of complementary action required. Examples of suitable insecticides include the following:

a) Pyrethroids such as permethrin, esfenvalerate, deltamethrin, cyhalothrin in particular lambda-cyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3-furylmethyl-(E)-(1R,3S)-2,2-dimethyl-3-(2-oxothiolan-3-ylidenemethyl) cyclopropane carboxylate;

b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chloropyrifos, phosalone, terbufos, fensulfothion, fonofos, phorate, phoxim, pyrimiphos-methyl, pyrimiphos-ethyl, fenitrothion or diazinon;

c) Carbamates (including aryl carbamates) such as pirimicarb, cloethocarb, carbofuran, furathiocarb, ethiofencarb, aldicarb, thiofurox, carbosulfan, bendiocarb, fenobucarb, propoxur or oxamyl;

d) Benzoyl ureas such as triflumuron, or chlorofluazuron;

e) Organic tin compounds such as cyhexatin, fenbutatin oxide, azocyclotin;

f) Macrolides such as avermectins or milbemycins, for example such as abamectin, avermectin, and milbemycin;

g) Hormones and pheromones;

h) Organochlorine compounds such as benzene hexachloride, DDT, chlordane or dieldrin;

i) Amidines, such as chlordimeform or amitraz;

j) Fumigant agents.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin can be employed. Alternatively insecticides specific for particular insect species/stages for example ovo-larvicides such as chlofentezine, flubenzimine, hexythiazox and tetradifon, moltilicides such as dicofol or propargite, acaricides such as bromopropylate, chlorobenzilate, or growth regulators such as hydramethylon, cyromazin, methoprene, chlorofluazuron and diflubenzuron may also be included in the compositions.

Examples of suitable synergists for use in the compositions include piperonyl butoxide, sesamax, safroxan and dodecyl imidazole.

Suitable herbicides, fungicides and plant-growth regulators for inclusion in the compositions will depend upon the intended target and the effect required.

An example of a rice selective herbicides which can be included is propanil, an example of a plant growth regulator for use in cotton is "Pix", and examples of fungicides for use in rice include blasticides such as blasticidin-S. The ratio of the compound of the invention to the other active ingredient in the composition will depend upon a number of factors including type of target, effect required from the mixture etc. However in general, the additional active ingredient of the composition will be applied at about the rate as it is usually employed, or at a slightly lower rate if synergism occurs.

The following Examples illustrate the invention. The compounds were identified and characterised by means of the melting points, nuclear magnetic resonance spectroscopy ($^1$H NMR $\delta$ (CDCl$_3$)), or mass spectroscopy.

EXAMPLE 1

This example illustrates the preparation of Compound No. 1 of Table I.

Step a

Preparation of 6-methoxy-2-mercaptobenzoxazole 2-amino-5-methoxyphenol hydrochloride (6 g) in 80 ml of water was stirred at room temperature while thiophosgene (3.92 g) was added dropwise as a solution in 30 ml of diethyl ether at a rate such that the resultant exotherm was controlled.

After the addition was completed, the two phase mixture was stirred vigorously for 8 hours. The organic layer was separated and the remaining aqueous layer was extracted with ethyl acetate. The combined organic extracts were washed with water, dried over anhydrous MgSO$_4$, filtered and evaporated under reduced pressure to yield a purple/pink solid. The solid was dissolved in ethyl acetate and washed with 2M sodium hydroxide. The aqueous layer was then acidified using 2M hydrochloric acid and extracted several times with ethyl acetate. The combined organic extracts were dried over anhydrous $MgSO_4$, filtered and the solvent removed under reduced pressure to give a purple/pink solid. This solid was recrystallised from hexane/ethyl acetate to give 2.3 g (30) of a pink solid.

NMR: 3.82 (s,3H); 6.85 (dd,1H); 6.93 (d,1H); 7.11 (d,1H).

Step b

Preparation of Compound No. 1 of Table I

The product of step a (1 g) was dissolved in acetone and potassium carbonate (0.83 g) was added in a single portion. 4-Bromo-1,1,2-trifluorobut-1-ene (1.69 g) was added to the reaction mixture and warmed to reflux.

After 2 hours the reaction mixture was allowed to cool, filtered to remove insoluble potassium salts and the filtrate was evaporated under reduced pressure to yield an orange oil. The oil was subjected to chromatography through silica using dichloromethane as eluent to yield 0.96 g (59%) of a yellow oil.

NMR: 2.8–3.0 (m,2H); 3.43 (t,2H), 3.82 (s,3H); 6.89 (dd,1H); 7.0 (d,1H); 7.48 (d,2H).

Compound Nos. 2, 3, 4, 6–8 and 9 of Table I were prepared by analogy using the preparative route of Example 1.

Compound No. 2

NMR: 2.81–3.0 (m,2H); 3.45 (t,2H); 7.04 (dt,1H); 7.19 (dd,1H); 7.53 (q,1H).
Melting point: 44°–46.5° C.

Compound No. 3

NMR: 2.83–3.01 (m,2H); 3.49 (t,2H); 7.02 (t,1H); 7.24 (m,1H); 7.40 (d,1H).

Compound No. 4

NMR: 2.85–3.15 (m,2H); 3.50 (t,2H); 7.70 (d,1H); 8.30 (dd,1H); 8.35 (d,1H).
$M^+$: 304.

Compound No. 6

NMR: 2.55 (s,3H); 2.90–3.10 (m,2H); 3.60 (t,2H); 7.20 (d,1H); 7.40 (s,1H); 7.60 (d,1H).
$M^+$: 273.

Compound No. 7

NMR: 2.82–3.01 (m,2H); 3.48 (t, 2H); 6.83 (dt, 1H); 7.13 (m, 1H).
$M^+$: 295.

Compound No. 8

NMR: 2.70–2.90 (m, 2H); 3.43 (t, 2H); 6.86 (d, 1H); 7.04 (d, 1H); 7.16 (t, 1H),; 8.05 (broad s, 1H).
$M^+$: 275.

Compound No. 9

NMR: 2.80–3.00 (m, 2H); 3.45 (t, 2H); 3.90 (s, 3H); 7.55 (d, 1H); 8.00 (dd, 1H); 8.08 (d, 1H).
$M^+$:317.
Melting point: 52.1°–53.2° C.

EXAMPLE 2

This example illustrates the preparation of compound no. 5 of Table I.

Compound No. 4 (1.3 g) was stirred in 20 ml of isopropanol at room temperature. Iron powder (2.6 g), 10 ml of water and one drop of concentrated hydrochloric acid were added and the reaction was heated to 80° C.

After 2 hours the reaction was allowed to cool, filtered and the filtrate was poured into 100 ml of water. This was extracted twice with 50 ml of ethyl acetate and the combined organic extracts were dried over anhydrous magnesium sulphate. The extracts were then filtered and the solvent removed under reduced pressure to give a brown oil. This oil was subjected to chromatography using silica and ethyl acetate/hexane (1:4) as the eluent. This yielded 700 mg (60%) of a brown oil.

Compound No. 5

NMR: 2.77–2.97 (m,2H); 3.42 (t,2H); 3.77 (s,2H); 6.54 (dd,1H); 6.77 (d,1H); 7.37 (d,1H).
$M^+$:274.

EXAMPLE 3

This example illustrates the preparation of Compound No. 10 of Table I.

Compound No. 5 (500 mg) was stirred in 5 ml of toluene. Acetic anhydride (194 mg) was added and the reaction was heated to reflux.

After 4 hours the reaction was allowed to cool. The solvent was evaporated under reduced pressure, toluene was added to the residue and the mixture evaporated to dryness under reduced pressure, to give a yellow oil. This oil was subjected to chromatography using silica and ethyl acetate/hexane (initially 1:4, increasing to 3:7), as the eluent. This yielded an off-white solid (380 mg, 66%).

NMR: 2.25 (s, 3H), 2.85–3.05 (m, 2H), 3.45 (t, 2H), 7.10 (dd, 1H), 7.30 (s, 1H), 7.50 (d, 1H), 8.10 (d, 1H).
Melting point: 90.5°–91.5° C.
$M^+$:316.

EXAMPLE 4

This example illustrates the preparation of Compound No. 11 of Table I.

Tertiary-butylnitrite (742 mg) and copper (II) chloride (578 mg) were stirred together in 15 ml of dry actonitrile at 0° C.

Compound No. 5 (1 g) was added slowly to the reaction in 15 ml of acetonitrile. On completing the addition the reaction was allowed to warm to room temperature.

After 3 hours the reaction was poured into 50 ml 2M hydrochloric acid and extracted with ethyl acetate (2×50 ml). The combined organic extracts were washed with 50 mls water, dried over anhydrous $MgSO_4$, filtered and the solvent removed under reduced pressure to give a a brown coil. This oil was subjected to chromtography using silica and ethyl acetate/hexane (1:4) as the eluent. This yielded an orange oil (864 mg, 81%).

NMR: 2.75–2.95 (m, 2H), 3.40 (t, 2H), 7.30 (d, 1H), 7.50 (d, 2H).
$M^+$: 293, 295.

EXAMPLE 5

This example illustrates the preparation of Compound No. 12 of Table I.

Compound No. 9 (1.5 g) and lithium hydroxide monohydrate (210 mg) were stirred together in a mixture of 30 ml of water and 30 ml of tetrahydrofuran.

After 4 hours the reaction was poured into 20 ml water. This was extracted twice with 30 ml of ether and the organic layer discarded. The aqueous layer was acidified to pH3, using 2M hydrochloric acid and extracted twice with 30 ml of ether. The combined organic extracts were dried over anhydrous MgSO4, filtered and the solvent removed under reduced pressure yielding a pink solid (1.38 g, 97%).

NMR CDCl3: 2.80–3.00 (m, 2H), 3.50 (t, 2H), 7.65 (d, 1H), 8.10 (d, 1H), 8.20 (s, 1H).

M+: 303.

Melting point: 95.7°–96.4° C.

EXAMPLE 6

This example illustrates the preparation of Compound No. 13 of Table I.

Step a

Preparation of 2-(3,4,4-trifluoro-butenylthio)-benzoxazole

2-Mercaptobenzoxazole (2 g), 4-bromo-1,1,2-trifluorobut-1-ene (2.75 g) and potassium carbonate (1 g) were stirred together in 40 ml of acetone and heated to reflux. After 2 hours the reaction mixture was allowed to cool, filtered to remove insoluble potassium salts and the filterate was evaporated under reduced pressure to yield 3.54 g of a brown oil which was used in step b without purification.

NMR: 2.82–3.00 (m,2H); 3.48 (t,2H); 7.26 (m,2H); 7.46 (dd,1H); 7.61 (dd, 1H).

Step b

Preparation of Compound 13 of Table I

The product of step a (1.5 g) was dissolved in 15 ml of ethanol and magnesium monoperoxyphthalic acid (2.86 g) in solution in 10 ml of water was added. The reaction mixture was heated to 65° C., held at this temperature for 2 hours, then allowed to cool. The reaction mixture was partitioned between 100 ml of 2M sodium bicarbonate and 20 ml of ethyl acetate. The aqueous layer was extracted with ethyl acetate (2×20 ml). The combined organic extracts were washed with sodium bicarbonate solution, dried over anhydrous magnesium sulphate, filtered and the solvent removed under reduced pressure to yield a yellow oil. The oil was subject to chromatography through silica using ethyl acetate/hexane (3:7) as eluent to yield a yellow oil which crystallised on standing. The solid was dissolved in 20 ml of ethyl acetate and washed with 2M sodium hydroxide. The organic layer was dried over anhydrous magnetisum sulphate, filtered and the filtrate was evaporated under reduced pressure to yield an off-white solid. The solid was recrystallised from hexane to yield 0.45 g of a white solid (28%).

NMR: 2.7–3.18 (m,2H); 3.58 (m,2H); 7.48 (m,2H); 7.67 (dd, 1H); 7.85 (dd,1H).

EXAMPLE 7

This Example illustrates the preparation of Compound No. 14 of Table I.

Step a

Preparation of 6-fluoro-2-mecapto-benzoxazole

2-Amino-5-fluorophenol [CAS:53981-24-1] (18.4 g) in 100 ml of water was stirred at room temperature while thiophosgene (16.8 g) was added dropwise as a solution in 100 ml of diethyl ether at such a rate that the resultant exotherm was controlled.

After the addition was complete, the two phase mixture was stirred for 2½ hours. The organic layer was separated and the remaining aqueous layer was extracted with ethyl acetate. The combined organic extracts were washed twice with water, and dried over anhydrous magnesium sulphate, filtered and the solvent removed under reduced pressure to yield 20 g (82%) of a black solid.

This black solid was then used to prepare Compound No. 14 of Table I using the method (by analogy) described in Example 6, steps a and b.

Compound No. 14

NMR: 2.72–3.15 (m,2H); 3.56 (dt,2H); 7.22 (dt,1H); 7.79 (q,1H); 7.37 (dd,1H).

Compound No. 15 of Table I was prepared by analogy with the preparative route of Example 7.

Compound No. 15

NMR: 2.55 (s,3H); 2.70–3.15 (m,2H); 3.57 (m,2H); 7.27 (d,1H); 7.45 (s,1H); 7.70 (d,1H).

M+: 289.

EXAMPLE 8

In order to illustrate the nematicidal properties of the compounds of formula (I), compounds from Table I were tested on root knot nematodes and cyst nematodes.

Methodology

Test A: Tomato plants (6–8 weeks old, variety 'Moneymaker') were planted out into soil infested with second stage juveniles of the root knot nematode *Meloidogyne incognita*. The soil was drenched with a composition of a compound of formula (I) (obtained by diluting 1 part of a solution of the compound in a 1:1 mixture of acetone and ethanol with 99 parts of water containing 0.05% of a wetting agent) at a rate of 2.5 or 1.25 ppm in a drench volume of 200 ml/kg of soil. The roots of the plants were examined after 3 weeks to determine the percentage reduction in the number of root knots compared with a control treatment omitting the compound. There were 3 replicates per treatment.

Test B: Tomato plants (6–8 weeks old, variety 'Moneymaker') were transplanted into soil infested with potato cyst nematode (*Globodera rostochiensis*). The soil was drenched with a composition of a compound of formula (I) (obtained by diluting 1 part of a solution of the compound in a 1:1 mixture of acetone and ethanol with 99 parts of water containing 0.05% of a wetting agent) at a rate of 10 or 20 ppm in a drench volume of 266 ml/kg of soil. The cysts were extracted from the soil after 8 weeks by flotation and percentage reduction in the number of cysts compared with a control treatment omitting the compound was determined. There were 5 replicates per treatment.

Test C: Cucumber plants (9 days old, variety 'Telegraph') were soil drenched with a composition of a compound of formula (I) (obtained by diluting 1 part of a solution of the compound in a 1:1 mixture of acetone and ethanol with 99 parts of water containing 0.05% of a wetting agent) at a rate of 40 ppm in a drench volume of 10 ml/45 g of soil. The plants were infested with second stage juveniles of the root knot nematode *Meloidogyne incognita* after the solution of the compound had been absorbed by the soil. Nematodes were applied to the roots in a solution of water. The roots of the plants were examined after 9 days to determine the percentage reduction in the number of root knots compared with a control treatment omitting the compound. There were 3 replicates per treatment.

The results are given in Table II. In the table a blank indicates less than 25% reduction, a hyphen indicates no test carried out at that rate.

TABLE II

| COMPOUND NO. | % ROOT KNOT REDUCTION | | | % CYST REDUCTION | |
|---|---|---|---|---|---|
| | APPLICATION RATE (PPM) | | | | |
| | 40 | 2.5 | 1.25 | 20 | 10 |
| 1 | 91 | 98 | 93 | 100 | 94 |
| 2 | 100 | 85 | 73 | 100 | 84 |
| 3 | 94 | 66 | | 65 | — |
| 4 | 100 | 90 | 66 | — | — |
| 6 | 100 | 95 | 83 | 100 | 69 |
| 7 | 100 | | | — | — |
| 8 | 100 | | | — | — |
| 9 | 97 | 57 | 45 | — | — |
| 10 | 97 | | | — | — |
| 11 | 97 | 97 | 89 | 100 | — |
| 12 | 99 | 60 | 43 | — | — |
| 13 | 99 | 35 | 35 | — | — |
| 14 | 97 | | | — | — |
| 15 | 94 | | | — | — |

The compounds of formula (I) display nematicidal activity against different types of nematodes including the cyst nematode. A further advantage is that the compounds are not phytotoxic to the target plant. Very little phytotoxicity was observed in the above tests. This is a particularly desirable feature when treating young plants and seeds.

The following examples demonstrate formulations suitable for applying the compounds of the present invention. The amount of ingredient is expressed in parts by weight or grams per litre as indicated. A * indicates a trademark.

EXAMPLE 9

This example demonstrates granules suitable for soil application. The granules can be made be standard techniques such as impregnation, coating, extrusion or agglomeration.

| | | % w/w |
|---|---|---|
| Impregnated granule | Active ingredient | 5 |
| | Wood Rosin | 2.5 |
| | Gypsum granules (20–40 mesh) | 92.5 |
| Coated granule | Active ingredient | 0.5 |
| | 'Solvesso'* 200 | 0.4 |
| | Calcium carbonate granules (30–60 mesh) | 99.1 |
| Slow release granule | Active ingredient | 10 |
| | Polyvinylacetate/vinyl chloride copolymer latex | 5 |
| | Attapulgus granules | 85 |

EXAMPLE 10

This example demonstrates formulations for use as a spray. The compounds can be formulated as wettable powders, water dispersible granules, suspension concentrates, emulsifiable concentrates, emulsions or microcapsule suspensions for application diluted in water.

| | | g/l |
|---|---|---|
| Emulsifiable concentrate | Active ingredient | 250 |
| | Calcium dodecyl-benzene sulphonate | 50 |
| | Nonyl phenol ethoxylate | 50 |
| | Alkylbenzene solvent | to 1 liter |
| | | % w/w |
| Wettable powder | Liquid active ingredient | 40 |
| | lignosulphonate dispersant | 5 |
| | silica | 25 |
| | sodium lauryl sulphate | 3 |
| | china clay (kaolin) | 27 |
| Microcapsule suspension | Liquid active ingredient | 250 |
| | toluene diisocyanate | 10 |
| | polymethylene polyphenyl isocyanate | 20 |
| | nonyl phenol ethoxylate | 6 |
| | lignosulphonate dispersant | 15 |
| | xanthan gum | 1 |
| | bentonite | 10 |
| | biocide 'Proxel'* | 0.1 |
| | sodium carbonate | 5 |
| | water | to 1 liter |

The microcapsule suspensions can be used as a spray, soil drench or as an intermediate to prepare slow release granules for application to the soil.

| | | g/l |
|---|---|---|
| Suspension concentrate | Solid active ingredient | 400 |
| | lignosulphonate dispersant | 50 |
| | sodium lauryl sulphate | 30 |
| | xanthan gum | 1 |
| | biocide 'Proxel'* | 0.1 |
| | bentonite | 10 |
| | water | to 1 liter |

This example demonstrates formulations suitable for use as seed treatments in conventional application machinery.

| | | % w/w |
|---|---|---|
| Dry seed treatment | Active ingredient | 20 |
| | dodecyl benzene | 3 |
| | Rubine Toner (dyestuff) | 2.7 |
| | Talc | 53.3 |
| | Silica | to 100% |

The suspension concentrate and microcapsule suspension of Example 5 can be used as flowable concentrates for seed treatment.

EXAMPLE 7

This example demonstrates the formulation of the compounds for electrostatic spraying.

| | g/l |
|---|---|
| Active ingredient | 200 |
| N-methylpyrollidone | 50 |
| Soyabean oil | 120 |

-continued

|  | g/1 |
| --- | --- |
| 'Solvesso'® 200 | to 1 liter |

CHEMICAL FORMULAE (Corresponding to Formulae Numbers in the Description)

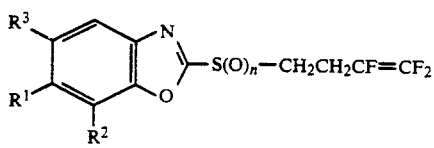
(I)

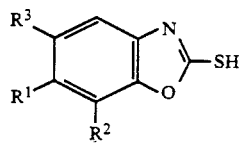
(II)

I claim:

1. A compound having the formula:

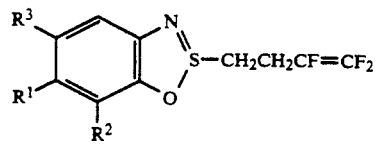

wherein $R_1$, $R_2$ and $R_3$ are independently hydrogen, nitro or $C_{1-3}$ alkoxy, provided that at least one of $R_1$, $R_2$ and $R_3$ is hydrogen, and that $R_1$, $R_2$ and $R_3$ are not all hydrogen.

2. A compound according to claim 1 wherein two of $R_1$, $R_2$, and $R_3$ are hydrogen and the third is nitro or $C_{1-3}$ alkoxy.

3. A compound according to claim 2 wherein one of $R_1$, $R_2$ and $R_3$ is nitro.

4. A compound according to claim 3 wherein $R_1$ is nitro.

5. A compound according to claim 2 wherein one of $R_1$, $R_2$, and $R_3$ is $C_{1-3}$ alkoxy.

6. A compound according to claim 5 wherein $R_1$ is $C_{1-3}$ alkoxy.

7. A compound according to claim 6 wherein $R_1$ is methoxy.

8. A nematicidal composition comprising an effective amount of a compound according to any of claims 1-7 and an inert diluent or carrier material and optionally a surface active agent.

9. A method for killing or controlling nematodes comprising applying to the locus of the pests or to a plant susceptible to attack by the pest an effective amount of a compound according to any of claims 1-7.

* * * * *

UNITED STATES PATENT AND TRADEMARK OFFICE
CERTIFICATE OF CORRECTION

PATENT NO. : 5,273,988
DATED : December 28, 1993
INVENTOR(S) : Michael D. Turnbull It is certified that error appears in the above-indentified patent and that said Letters Patent is hereby corrected as shown below:

Title Page:

Item [30] "Foreign Application Priority Data" should correctly read:

March 28, 1991 (GB) United Kingdom....9106655
    March 28, 1991 (GB) United Kingdom....9106656

Signed and Sealed this

Thirteenth Day of December, 1994

Attest:

BRUCE LEHMAN

*Attesting Officer*      *Commissioner of Patents and Trademarks*